United States Patent [19]

Johnston et al.

[11] Patent Number: 5,126,488
[45] Date of Patent: Jun. 30, 1992

[54] 2β,19-METHYLENEAMINO BRIDGED STEROIDS AS AROMATASE INHIBITORS

[75] Inventors: J. O'Neal Johnston, Milford; Joseph P. Burkhart, West Chester; Norton P. Peet, Cincinnati, all of Ohio

[73] Assignee: Merrell Dow Pharmaceuticals Inc., Cincinnati, Ohio

[21] Appl. No.: 621,183

[22] Filed: Nov. 30, 1990

[51] Int. Cl.$^5$ .................. C07J 71/00; C07J 51/00; A61K 31/58
[52] U.S. Cl. .................. 514/176; 540/49; 540/91; 552/505
[58] Field of Search .................. 540/49, 91; 514/176; 435/184; 552/505

[56] References Cited

U.S. PATENT DOCUMENTS 4,322,416  3/1982  Metcalf et al. .................. 540/91

OTHER PUBLICATIONS

Johnson, et al., Endocrinology 115(2), 1984 pp. 776 to 785.
Burkhart, Steroids 45(3,4), 1985 pp. 357-374.
Lan-Hargest et al., *Tetrahedron Letters*, 28, 6117 (1987).
Grenway et al., *Biochemistry International*, 20, 591 (1990).
Eggleston et al., *Chemical Abstracts*, 109, 139666j (1988).

*Primary Examiner*—Robert T. Bond
*Attorney, Agent, or Firm*—John J. Kolano

[57] ABSTRACT

The present invention is directed to 2β,19-(methyleneamino)androst-4-ene-3,17-dione which has the formula

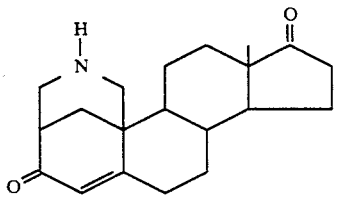

and the corresponding 17β-ol which are useful as aromatase inhibitors. The compounds are prepared by the cyclization of an appropriate 19-[N-protected-[(2-methoxyethoxy)methylamino] steroid using titanium tetrachloride followed by, if desired, selective reduction of the 17-ketone.

6 Claims, No Drawings

2β,19-METHYLENEAMINO BRIDGED STEROIDS AS AROMATASE INHIBITORS

BACKGROUND OF THE INVENTION

The estrogen hormones, estrone and estradiol, are involved in many physiological processes. The formation of these steroids is regulated by a number of enzymes. The enzyme aromatase is the rate limiting enzyme in the nonreversible conversion of the androgen hormones, testosterone and androstenedione, to the estrogen hormones, estradiol and estrone. Compounds which are aromatase inhibitors can thus regulate or inhibit androgen to estrogen conversion, and have therapeutic utility in treating clinical conditions potentiated by the presence of estrogens.

DETAILED DESCRIPTION OF THE INVENTION

The present invention is directed to 2,19-methyleneamino bridged steroid compounds which are steroidal aromatase inhibitors, their related intermediates, their use as aromatase inhibitors, and the process for their preparation. More specifically, this invention relates to the compounds represented by the following structure:

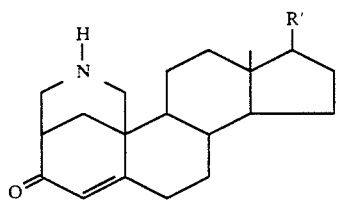

wherein R' is =O or β—OH.

In describing the compounds of the present invention, they have been referred to generally as 2β,19-methyleneamino bridged steroids and similar terminology is used below in referring to some of the specific intermediate compounds used to prepare the compounds of the present invention. This terminology indicates that the group —CH$_2$—NH— connects the 2- and 19-positions in a regular steroid molecule with the carbon attached to the 2-position of the steroid and the nitrogen attached to the 19-position. The β-designation is further used in connection with the 2-position to provide an explicit indication that the bridge is attached there on the β-face.

The compounds of the present invention can be obtained by the internal cyclization of an appropriate 19-(substituted amino)steroid wherein the oxo groups at the 3- and 17-positions are protected as silyl enol ethers. More particularly, the compounds of the present invention are prepared by the reaction of a steroid of the following structure:

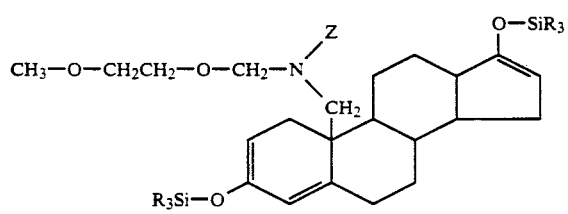

wherein Z is an amine protecting group and R is C$_{1-4}$ alkyl, with titanium tetrachloride in an inert solvent at low temperature followed by removal of the amine protecting group. In the initial cyclization step and work up, the silyl enol ether protecting groups are also removed and the initial material obtained corresponds to the desired product except that the amine protecting group is still present. The cyclization is carried out at about −20° C. and the solvent used is a halogenated hydrocarbon, preferably methylene chloride. The 3- and 17-oxygens are preferably protected as the trimethylsilyl enol ethers.

The amine protecting group, Z, is a group that can be removed readily under mild conditions, without affecting the rest of the molecule. The amine is preferably protected as the amide with trifluoroacetic anhydride. The resulting trifluoroacetyl protecting group can then be removed at room temperature using a weak base such as potassium carbonate in an alkanol solvent such as methanol. The 3-keto-17β-hydroxy compound of the present invention can be obtained by the selective reduction of the 3,17-diketone using lithium tri(t-butoxy)aluminum hydride.

The starting material shown above can be readily obtained starting from 19-(trifluoroacetamido)androst-4-ene-3,17-dione. This amide is reacted with (2-methoxyethoxy)methyl chloride [MEM-chloride] in the presence of a strong base such as potassium hydride to give the corresponding N[(2-methoxyethoxy)methyl]-substituted compound. The desired silyl protection at the 3- and 17-positions is then introduced by reacting the 3,17-diketone with a strong base (for example, lithium diisopropylamide) in the presence of a trialkylsilyl halide such as trimethylsilyl chloride in an inert solvent such as tetrahydrofuran. This reaction gives the desired intermediate referred to above.

The compounds of the present invention are inhibitors of aromatase. As aromatase inhibitors, they are useful in treating hyperestrogenemia. The compounds are useful in controlling abnormally high levels of estrogens, both when the high levels observed are relatively steady, or when there are brief surges of elevated levels occurring as part of cyclical body functions. Both females and males can be treated, although obviously, the level of estrogens which would be considered high in males would be much lower than the amount considered high in females. The compounds are also useful as anti-fertility agents to prevent ovulation or implantation in females, or to reduce the mating behavior in males where brain aromatization is required for such behavior. The compounds further have value in treating gynecomastia, male infertility resulting from elevated estrogen levels, and hyperestrogenemia, which may precede myocardial infarction. The compounds also may be used to treat breast cancer and other various estrogen-induced or estrogen-stimulated tumors and hyperplastic tissue disorders.

To achieve their desired effect, the compounds of the present invention may be administered orally, parenterally, for example, intravenously, intraperitoneally, intramuscularly, or subcutaneously, including the injection of the active ingredient directly into tissue or tumor sites, to a patient in need of treatment. The term patient is taken to mean a warm-blooded animal, for example, mammals such as humans, primates, cattle, dogs, cats, horses, sheep, mice, rats and pigs. The compounds may also be administered in the form of a pharmaceutical preparation, and may further be incorporated into sustained delivery devices. The amount of compound administered will vary over a wide range and be any effective amount. Depending on the patient to be treated, the condition to be treated, and mode of administration, the effective amount of compound administered will vary from about 0.01 to 150 mg/kg of body weight per day, and preferably from about 0.1 to 50 mg/kg body weight per day.

For oral administration, the compounds can be formulated into solid or liquid preparations, such as capsules, pills, tablets, troches, powders, solutions, suspensions, or emulsions. The solid unit dosage forms can be a capsule which can be of the ordinary gelatin type containing the active compound and a carrier, for example, lubricants and inert filler such as lactose, sucrose and corn starch. In another embodiment, an active compound of the invention can be tableted with conventional tablet bases such as lactose, sucrose and corn starch in combination with binders such as acacia, corn starch, alginic acids and a lubricant such as stearic acid or magnesium stearate.

For parenteral administration the compounds may be administered as an injectable dosage of a solution or suspension of the compound in a physiological acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose and related sugar solutions, ethanols and glycols, such as propylene glycol or polyethylene glycol are preferred liquid carriers, particularly for injectable solutions.

The compounds can be administered in the form of a cutaneous patch, a depot injection, or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for example, Silastic ®, silicone rubber manufactured by Dow Corning Corporation. Further information on suitable pharmaceutical carriers and formulation techniques are found in standard texts such as *Remington's Pharmaceutical Sciences*, Mack Publishing Company, Easton, Pa.

The following are illustrative of specific pharmaceutical formulations, suitable for oral administration, which may be employed in practicing the present invention:

| TABLET | |
|---|---|
| (a) 2$\beta$,19-(Methyleneamino)androst-4-ene-3,17-dione | 150 g |
| (b) Lactose | 1.216 Kg |
| (c) Corn starch | 0.3 Kg |

Mix the active ingredient, the lactose and corn starch uniformly. Granulate with 10% starch paste. Dry to a moisture content of about 2.5%. Screen through a No. 12 mesh screen. Add and mix the following:

| (a) Magnesium Stearate | 0.015 Kg |
|---|---|

| -continued | |
|---|---|
| (b) Corn starch qs ad | 1.725 Kg |

Compress on a suitable tablet machine to a weight of 0.115 g/tablet.

| SOFT GELATIN CAPSULE | |
|---|---|
| (a) 2$\beta$,19-(Methyleneamino)androst-4-ene-3,17-dione | 0.50 Kg |
| (b) Polysorbate 80 | 0.25 Kg |
| (c) Corn oil qs ad | 25.0 Kg |

Mix and fill into 50,000 soft gelatin capsules.

The activity of the present compounds in the inhibition of aromatase is demonstrated by using laboratory methods similar to procedures described in U.S. Pat. No. 4,322,416, and as published in Johnston et al., *Endocrinology* 115:776, 1984, and Burkhart et al., *Steroids* 45:357, 1985.

In this assay, the inhibitor is preincubated with enzyme prior to assaying for activity in the presence of high substrate levels. A time-related decrease in enzyme activity can be indicative of a preferred mode of inhibition.

In the time-dependent assay, an amount of the enzyme inhibitor in 100 $\mu$l of the assay buffer described above which will provide assay concentrations which are usually between 1 nM and 10 $\mu$m are added to 35 ml centrifuge tubes containing 600 $\mu$l of the NADPH generating system. The preincubation is started by the addition of 700 $\mu$l of aromatase preparation, usually 300–800 $\mu$g of microsomal protein per ml of assay buffer. These preparations are mixed using a vortex mixer and incubated for 0, 5, 10 or 20 minutes at 25° C. Then 100 $\mu$l of androstenedione (~6.8 $\mu$M) containing 1$\beta$-$^3$H androstenedione is added in assay buffer to provide an assay concentration of substrate (0.55 $\mu$M) which is at least ten times the $K_m$ of androstenedione (0.04 $\mu$M). Following vortexing, the enzyme incubation is continued for 10 minutes before being terminated by the addition of chloroform. The amount of radioactivity in the aqueous fraction is determined by scintillation procedures. The enzymatic activity for each concentration of inhibitor at each time period of preincubation is calculated as a percent of the "0" minute vehicle control arbitrarily set at 100%. Therefore, the present enzyme inhibition is expressed as a percentage: (100 percent minus percent enzyme activity with inhibitor present).

Enzyme kinetic analysis utilized Kitz-Wilson plots for time-dependent assays. These analyses provide estimates of apparent $K_i$ of inactivation which represents the inhibitor concentration required to produce half-maximal rate of enzyme inactivation. The pseudo first-order rate constant for enzyme inactivation ($k_{cat}$) and the half-time of inactivation ($\tau_{50}$) of infinite inhibitor concentrations were determined. The ratio of $k_{cat}/K_i$ (inactivation) provides an index number which increases with increased efficiency of enzyme inactivation and increased inhibitor affinity for the enzyme active site. Using this test, the following results were observed for the compound 2$\beta$,19-(methyleneamino)androst-4-ene-3,17-dione:

$K_i$(nM) = 259
$\tau_{50}$(min) = 2.66
$k_{cat}/K_i$ = 16,760

The following examples are presented to illustrate the present invention but they should not be construed as limiting it in any way.

EXAMPLE 1

A potassium hydride dispersion (35 wt. % in mineral oil, 952 mg, 8.30 mmole), under argon, was washed with hexane (3 ×15 ml) to remove the mineral oil, the remnants of hexane were removed with a stream of argon and tetrahydrofuran (40 ml) added. To the stirred suspension of potassium hydride in tetrahydrofuran was added a solution of 19-(trifluoroacetamido)androst-4-ene-3,17-dione [Lovett et al., *J. Med. Chem.*, 27, 734 (1984)] (3.00 g, 7.55 mmole) in tetrahydrofuran (40 ml). After the cessation of gas evolution, 18-crown-6 (2.99 g, 11.32 mmole) was added followed by (2-methoxyethoxy)methyl chloride (1.21 ml, 10.57 mmole), the reaction stirred at room temperature for 1 hour and then refluxed for 25 hours. The reaction was allowed to cool to room temperature and then concentrated to about ¼ the original volume. To the residue was added ethyl ether (100 ml) followed by methylene chloride (50 ml) and then water (100 ml)/saturated aqueous potassium chloride (100 ml). The layers were separated and the organics washed with satd aqueous potassium chloride (3×100 ml), dried ($Na_2SO_4$) and concentrated to give a yellow oil. Flash chromatography (7 ×14 cm silica gel column) eluting with ethyl acetate/hexane (65:35) gave 19-[N-[(2-methoxyethoxy)methyl]trifluoroacetamido]androst-4-ene-3,17-dione (1.09 g, 30%) as an oily, yellow foam.

HRMS calculated for $C_{25}H_{35}F_3NO_5$ ($MH^+$)=486.2467; found $MH^+$=486.2445; error= −4.5 ppm.

$^1H$ NMR ($CDCl_3$) δ 6 5.96(s, 1H, vinyl), 4.87 and 4.72(pr d, 2H, J=11 Hz, $NCH_2O$), 4.32 and 3.91 (pr d, 2H, J=14 Hz, $CH_2N$), 3.57 (br s, 4H, $OCH_2CH_2O$), 3.39 (s, 3H, $OCH_3$), 0.94 (s, 3H, 18—$CH_3$).

IR (thin film) 2935, 1736, 1700, 1670, 1450, 1195, 1150, 1090 $cm^{-1}$.

MS (CI, $CH_4$) m/z (rel intensity) 486 ($MH^+$, 100), 410 (65), 392 (12), 89 (19). MS (EI) m/z (rel intensity) 485 ($M^+$, 5), 409 (28), 368 (9), 360 (9), 284 (14), 89 (100), 59 (73), 49 (14).

EXAMPLE 2

To a stirred solution of diisopropylamine (1.03 ml, 7.34 mmole) in tetrahydrofuran (65 ml) under argon and cooled to −20° C. was added n-butyl lithium (2.76 ml of a 2.42M solution in hexane, 6.67 mmole). After 9 minutes, a cooled (−20° C.) solution of trimethysilyl chloride (2.82 ml, 22.24 mmole) in tetrahydrofuran (10 ml) was added slowly. After 2 minutes more, a cooled (−20° C.) solution of 19-[N-[(2-methoxyethoxy)methyl]trifluoroacetamido]androst-4-ene-3,17-dione (1.08 g, 2.22 mmole) in tetrahydrofuran (10 ml) was added dropwise. The reaction was stirred at −20° C. for 30 minutes and then allowed to warm slowly to room temperature. After 30 minutes at room temperature, triethylamine (10 ml) was added then ethyl ether (350 ml) and the organics washed with saturated sodium bicarbonate (2×100 ml), 150 ml of water-saturated aqueous sodium bicarbonate (2:1) and finally 100 ml of brine-saturated aqueous sodium bicarbonate (3:1). Drying ($Na_2SO_4$) and concentration gave 19-[N-[(2-methoxyethoxy)-methyl]trifluoroacetamido]-3,17-bis(-trimethylsilyloxy)androsta-2,4,16-triene (quantitative) as a pale-yellow, viscous oil.

$^1H$ NMR ($CDCl_3$) δ 5.45-5.49 (m, 1H, vinyl), 4.94 and 4.86 (pr d, 2H, J=11 Hz, $OCH_2N$), 4.52-4.60 (m, 1H, vinyl), 4.46-4.52 (m, 1H, vinyl), 3.84 and 3.78 (pr d, 2H, J=15 Hz, $CH_2N$), 3.55 (s, 4H, $OCH_2CH_2O$), 3.38 (s, 3H, $OCH_3$), 0.84 (s, 3H, 18—$CH_3$), 0.19 and 0.15 (pr s, $SiCH_3$).

EXAMPLE 3

To a stirred solution of titanium tetrachloride (6.66 ml of a 1.0M solution in methylene chloride, 6.66 mmole) in additional methylene chloride (25 ml) under argon and cooled to −20° C. was rapidly added a solution of 19-[N-[(2-methoxyethoxy)methyl]trifluoroacetamido]-3,17-bis(trimethylsilyloxy)androsta-2,4,16-triene (2.22 mmole) in methylene chloride (3 ml). After 1.5 hours at −20° C., the reaction was poured into satd aqueous sodium bicarbonate (150 ml) and extracted with methylene chloride (150 ml, then 2×100 ml). The combined organics were washed with saturated aqueous sodium bicarbonate (150 ml), water (100 ml), 1N hydrochloric acid (2×100 ml) and brine (75 ml). Drying ($Na_2SO_4$) and concentration gave an oily, yellow solid. Filtration through a plug of silica gel using ethyl acetate/hexane (75:25) as the eluent removed the remaining titanium salts and concentration of the filtrates gave crude product. Flash chromatography (4×12 cm silica gel column) eluting with ethyl acetate/hexane (55:45) gave 2β,19-[N-trifluoroacetyl(methyleneamino)]androst-4-ene-3,17-dione (86 mg, 9%) as a white solid.

$^1H$ NMR ($CDCl_3$) δ 6.01-6.06 (m, 1H, vinyl), 4.62 (ddd, 1H, J=12.8, 2.2, 2.2 Hz, ¼ $CH_2NCH_2$), 4.00-4.10 (m, 1H, ¼ $CH_2NCH_2$), 3.28 (dd, 1H, J=14.0, 3.2 Hz, ¼ $CH_2NCH_2$), 2.92 (d, 1H, J=12.8 Hz, ¼ $CH_2NCH_2$) 0.95 (s, 3H, 18—$CH_3$).

$^{13}C$ NMR ($CDCl_3$) δ 219.8, 197.9, 165.5, 156.9 (q, $COCF_3$), 128.6, 116.2 (q, $CF_3$). Downfield signals only.
$^{19}F$ NMR ($CDCl_3$) δ −68.62 (s, $CF_3$).

IR (film) 2926, 2882, 2858, 1736, 1692, 1666, 1606, 1202, 1180, 1142 $cm^{-1}$.

MS (CI, $CH_4$) m/z (rel intensity) 410 ($MH^+$, 100). MS(EI) m/z (rel intensity) 410 (12), 409 ($M^+$, 36), 43 (100).

EXAMPLE 4

To a stirred solution of β,19-[N-trifluoroacetyl(methyleneamino)]androst-4-ene-3,17-dione (72 mg, 0.18 mmole) in methanol (15 ml) was added 10% aqueous potassium carbonate (2.5 ml). After 2.5 hours, the reaction was concentrated to about ⅓ the original volume and poured into 5% aqueous potassium carbonate (25 ml)/methylene chloride (35 ml). The layers were separated and the aqueous layer extracted with additional methylene chloride (2×15 ml). The combined organics were washed with 5% aqueous potassium carbonate (25 ml) followed by 20 ml of brine/5% potassium carbonate (3:1). Drying ($Na_2SO_4$) and concentration gave an oil which was flash chromatographed (3×13 cm silica gel column), eluting with methanol/chloroform (7:93) to give β,19-(methyleneamino)androst-4-ene-3,17-dione as a white solid (38 mg, 69%); mp=168°-171° C.

HRES calculated for $C_{20}H_{27}NO_2$ (M+)=313.2042; found $M^+$ =313.2030; error= −3.8 ppm.

$^1H$ NMR ($CDCl_3$) δ 6.15 (d, 1H, J=1.9 Hz, vinyl), 2.98 (ddd, 1H, J=13.5, 1.9, 1.9 Hz, ¼ $CH_2NCH_2$), 2.90 (d, 1H, J=13.0 Hz, ¼ $CH_2NCH_2$), 2.78 (dd, 1H, J=13.0, 2.4 Hz, ¼ $CH_2NCH_2$), 2.73 (dd, 1H, J=13.5, 3.4 Hz, ¼ $CH_2NCH_2$), 0.91 (s, 3H, 18—$CH_3$).

$^{13}$C NMR (CDCl$_3$) δ 220.1, 201.7, 166.4, 129.4, 51.3, 51.2, 47.4, 47.3, 45.8, 44.0, 40.5, 37.7, 35.7, 35.0, 32.2, 31.5, 29.5, 21.7, 20.3, 13.6.

IR (film) 3328, 2928, 2858, 1738, 1664, 1610, 1454, 1220, 918, 730 cm$^{-1}$.

MS (CI, CH$_4$) m/z (rel intensity) 314 (MH$^+$, 100). MS(EI) m/z (rel intensity) 314 (MH$^+$, 12), 313 (M$^+$, 15), 43 (100).

This compound has the following structure:

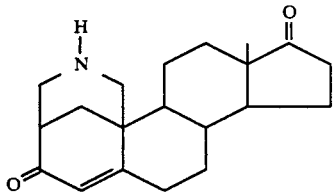

EXAMPLE 5

2β,19-(Methyleneamino)androst-4-ene-3,17-dione (1 mmole) is reacted with 2.3 mmoles of lithium tri-(t-butoxy)aluminum hydride (used as a 1M solution in tetrahydrofuran) in 8 ml of tetrahydrofuran at 0° C. for 45 minutes. The reaction mixture is quenched with water and then acidified with 10% hydrochloric acid. The resulting mixture is extracted with methylene chloride, the organic extracts are discarded and the aqueous layer is made basic with sodium bicarbonate. The aqueous layer is then extractd repeatedly with methylene chloride and the combined organic extracts are washed with aqueous sodium bicarbonate followed by brine and dried over sodium sulfate. Evaporation of the solvent followed by chromatography gives pure 2β,19-(methyleneamino)-17β-hydroxyandrost-4-en-3-one.

What is claimed is:

1. A compound of the formula:

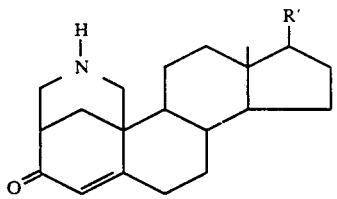

wherein R' is =O or β—OH.

2. A compound according to claim 1 which is 2β,19-(methyleneamino)androst-4-ene-3,17-dione.

3. A method of inhibiting aromatase activity which comprises contacting an aromatase enzyme in vivo with an effective aromatase-inhibiting amount of a compound according to claim 1.

4. A method of treating hyperestrogenemia which comprises administering to a patient having said condition an effective aromatase-inhibiting amount of a compound according to claim 1.

5. A method of treating breast cancer which comprises administering to a patient having said condition an effective aromatase-inhibiting amount of a compound according to claim 1.

6. A pharmaceutical composition having aromatase inhibiting activity, in a dosage unit form, comprising a pharmaceutical carrier and a compound according to claim 1.

* * * * *

UNITED STATES PATENT AND TRADEMARK OFFICE
CERTIFICATE OF CORRECTION

PATENT NO. : 5,126,488

DATED : June 30, 1992

INVENTOR(S) : J.O'Neal Johnston, N.P. Peet, J.P. Burkhart

It is certified that error appears in the above-identified patent and that said Letters Patent is hereby corrected as shown below:

```
Column 6, line 46, "of β,19-" should read -- 2β,19- --.
Column 6, line 60, "give β,19-" should read -- give 2β,19- --.
```

Signed and Sealed this

Twenty-eighth Day of September, 1993

Attest:

BRUCE LEHMAN

*Attesting Officer*         *Commissioner of Patents and Trademarks*